US00PP23625P2

(12) United States Plant Patent
Sakazaki

(10) Patent No.: US PP23,625 P2
(45) Date of Patent: May 21, 2013

(54) ***CAMPANULA* PLANT NAMED 'USCAMP08'**

(50) Latin Name: *Campanula punctata*
Varietal Denomination: USCAMP08

(75) Inventor: Ushïo Sakazaki, Hikone (JP)

(73) Assignee: Amerinova Properties LLC., Bonsall, CA (US)

( * ) Notice: Subject to any disclaimer, the term of this patent is extended or adjusted under 35 U.S.C. 154(b) by 9 days.

(21) Appl. No.: 13/317,206

(22) Filed: Oct. 12, 2011

(51) Int. Cl.
*A01H 5/00* (2006.01)

(52) U.S. Cl.
USPC ..... Plt./414

(58) Field of Classification Search ..... Plt./414
See application file for complete search history.

*Primary Examiner* — Susan McCormick Ewoldt
(74) *Attorney, Agent, or Firm* — Cassandra Bright

(57) ABSTRACT

A new and distinct *Campanula* cultivar named 'USCAMP08' is disclosed, characterized by vigorous plant growth, large, red-purple flowers. The new variety is a *Campanula*, normally produced as an outdoor ornamental plant for containers or gardens.

1 Drawing Sheet

Latin name of the genus and species: *Campanula punctata*.
Variety denomination: 'USCAMP08'.

BACKGROUND OF THE INVENTION

The new cultivar was discovered as a result of a planned breeding program directed by the inventor, Ushio Sakazaki, a citizen of Japan. The seed parent is an unnamed, unpatented *Campanula punctata* and the pollen parent is the unpatented variety *Campanula punctata* 'Kurokawae'. The cross resulting in 'USCAMP08' was made Jun. 15, 2002. The new variety was discovered Sep. 18, 2003, by the inventor in a non-commercial nursery in Hikone, Japan.

Asexual reproduction of the new cultivar 'USCAMP08' by vegetative division was first performed Oct. 10, 2003 at a non-commercial nursery in Hikone, Japan. Multiple generations have since been produced and have shown that the unique features of this cultivar are stable and reproduced true to type in successive generations. The new cultivar was first sold and made available to the public in April 2011.

SUMMARY OF THE INVENTION

The cultivar 'USCAMP08' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'USCAMP08' These characteristics in combination distinguish 'USCAMP08' as a new and distinct *Campanula* cultivar:

1. Vigorous growth habit.
2. Large flowers
3. Red-purple flower color.

PARENT COMPARISON

Plants of the new cultivar 'USCAMP08' are similar to plants of the seed parent, *Campanula punctata*, unnamed, in most horticultural characteristics, however, plants of the new cultivar 'USCAMP08' produce flowers over a longer period than the seed parent. Plants of 'USCAMP08' are overall shorter than the seed parent, however, the new variety grows faster than the seed parent.

Plants of the new cultivar 'USCAMP08' are similar to plants of the pollen parent *Campanula punctata* 'Kurokawae' in most horticultural characteristics, however, plants of the new cultivar 'USCAMP08' are overall taller than the pollen parent. Additionally, the new variety has grows more vigorously than the pollen parent.

COMMERCIAL COMPARISON

'USCAMP08' can be compared to the commercial variety *Campanula takesimana* 'Elizabeth', unpatented. The two varieties are similar in most horticultural characteristics, however, plants of 'USCAMP08' begin blooming earlier than plants of 'Elizabeth'. Additionally, plants of the new variety are shorter and produce darker colored flowers than 'Elizabeth'.

'USCAMP08' can be compared to the commercial variety *Campanula* 'Pantaloons' U.S. Plant Pat. No. 13,282. The two varieties are similar in most horticultural characteristics, however, plants of 'USCAMP08' are shorter and produce single flowers, compared to the double flowers of 'Pantaloons'. Additionally the flower color differs, 'Pantaloons' has a lighter, more purple shaded flower than 'USCAMP08.'

BRIEF DESCRIPTION OF THE PHOTOGRAPH

The accompanying photograph in FIG. 1 illustrates in full color a of typical plant of 'USCAMP08' grown in a poly house, in Bonsall, Calif., in a commercial 6 inch container. The photographs was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'USCAMP08' plants grown in a poly house, in Bonsall, Calif., in a commercial 6 inch container. The growing temperature ranged from 60° F. to 75° F. daytime and 50° F. to 60° F. at night. No chemical treatments were given. Measurements and numerical values represent averages of typical plant types.

Botanical classification: *Campanula punctata* 'USCAMP08'.

PROPAGATION

Time to initiate roots during summer: Approximately 4 days at temperatures between 18° C. and 32° C.

Time to initiate roots during winter: Approximately 5 days at temperatures between 18° C. and 24° C.

Time to produce a rooted cutting: 34 to 37 days.

Root description: Fibrous, moderate to free branching, rhizomes present. Rhizomes approximately 0.4 cm thick, colored near Greyed-Orange 164D.

PLANT

Pot size of plant described: 6 inch pot.

Age of plant described: Approximately 10 Weeks.

Growth habit: Low mounding.

Height: Approximately 15 cm.

Plant spread: Approximately 32 cm.

Stem characteristics:

Length of stems: Approximately 18 cm.

Diameter of stems: Approximately 0.3 cm.

Quantity of stems per plant: Approximately 25 basally emerging stems, lateral branching rare.

Texture of stems: Hispid, hairs minute, not dense.

Color of stems: Near RHS Green 143A, sometimes flushed with Greyed-Purple 187B.

FOLIAGE

Leaf:

*Arrangement*.—Alternate.

*Quantity*.—Approximately 10 per main branch.

*Average length*.—Approximately 4.5 cm.

*Average width*.—Approximately 2.2 cm.

*Shape of blade*.—Broad lanceolate.

*Apex*.—Acute

*Base*.—Broad attenuate.

*Margin*.—Crenulate.

*Texture of top surface*.—Pubescent.

*Texture of bottom surface*.—Pubescent.

*Leaf internode length*.—Approximately 1.5 to 3.5 cm.

*Color*.—Young foliage upper side: Near RHS Green 137B. Young foliage under side: Near RHS Green 137C. Mature foliage upper side: Near RHS Green 137A. Mature foliage under side: Near RHS Green 137C.

*Venation*.—Type: Pinnate. Venation color upper side: Near Yellow-Green 144C. Venation color under side: Near Yellow-Green 145A.

*Petiole*.—Sessile.

FLOWER

Natural flowering season: Spring and Summer.

Begins flowering after how many months/weeks:

Inflorescence type and habit: Campanulate flowers, occurring either singly from leaf axils, or occurring as a cyme composed of 3 to 5 flowers.

*Cyme*.—Width: Approximately 6.0 cm. Height: Approximately 5.5 cm.

Rate of flower opening: Approximately days from bud to fully opened flower.

Flower longevity on plant: Days, after fully opened.

Quantity of flowers: Approximately 30 open flowers per mature plant.

Flower size:

*Diameter*.—Approximately 2.7 cm.

*Length*.—Approximately 4.5 cm.

Peduncle:

*Length*.—Approximately 2.0 cm.

*Diameter*.—Approximately 0.1 cm.

*Color*.—Near RHS Greyed-Purple 187A.

*Texture*.—Hirsute.

Pedicel:

*Length*.—Range from Approximately 2.0 cm.

*Diameter*.—Approximately 0.1 cm.

*Color*.—Near RHS Green 138A, flushed with Greyed-Purple 187A.

*Texture*.—Softly pubescent.

Corolla:

*Petal arrangement*.—Fused corolla.

*Shape*.—Campanulate, lobes approximately 0.7 cm deep.

*Margin*.—Entire.

*Apex*.—Acute.

*Petal quantity*.—5.

*Texture*.—Exterior glabrous, interior pubescent.

Color:

*Petals*.—When opening: Inner surface: Near RHS Red-Purple 59D. Outer surface: Near RHS Red-Purple 60D. Fully opened: Inner surface: Near RHS Red-Purple 59D. Outer surface: Near RHS Red-Purple 59D. Aging: Inner surface: Near RHS Greyed-Purple 185C. Outer surface: Near RHS Greyed-Purple 185D.

Bud:

*Shape*.—Puffy, elongated sphere.

*Length*.—Approximately 1.8 cm.

*Diameter*.—Approximately 1.2 cm.

*Color*.—Near RHS Red-Purple 59B.

Sepals:

*Quantity*.—5.

*Length*.—Approximately 1.2 cm.

*Width*.—Approximately 0.5 cm.

*Shape*.—Deltoid.

*Color*.—Interior Surface: Near RHS Green 143C. Exterior Surface: Near RHS Green 143C.

*Texture*.—Pubescent.

Fragrance: None.
Persistence: Flower persistent.

REPRODUCTIVE ORGANS

Stamens:
*Number.*—5.
*Filament length.*—Approximately 0.3 cm.
*Filament color.*—Near RHS White 155C.
Anthers:
*Length.*—0.7 cm.
*Shape.*—Linear.
*Color.*—Near RHS White 155A.
*Pollen.*—Color: Near RHS White 155A. Quantity: Scant.
Pistil:
*Number.*—1.
*Length.*—Approximately 2.5 cm.
*Style.*—Length: Approximately 0.8 cm. Color: Near RHS White 155D.
*Stigma.*—Shape: Linear. Length: Approximately 1.4 cm. Color: Near RHS White 155D. Ovary Color: Near RHS White 155D.

OTHER CHARACTERISTICS

Seeds and fruits: Not observed to date.
Disease/pest resistance: Neither resistance nor susceptibility to normal pests and diseases of *Campanula* observed to date.
Drought tolerance and temperature tolerance: Hardy perennial to −10° C. Upper temperature tolerance to at least 40° C. No tolerance for drought.

What is claimed is:

1. A new and distinct cultivar of *Campanula* plant named 'USCAMP08' as herein illustrated and described.

* * * * *

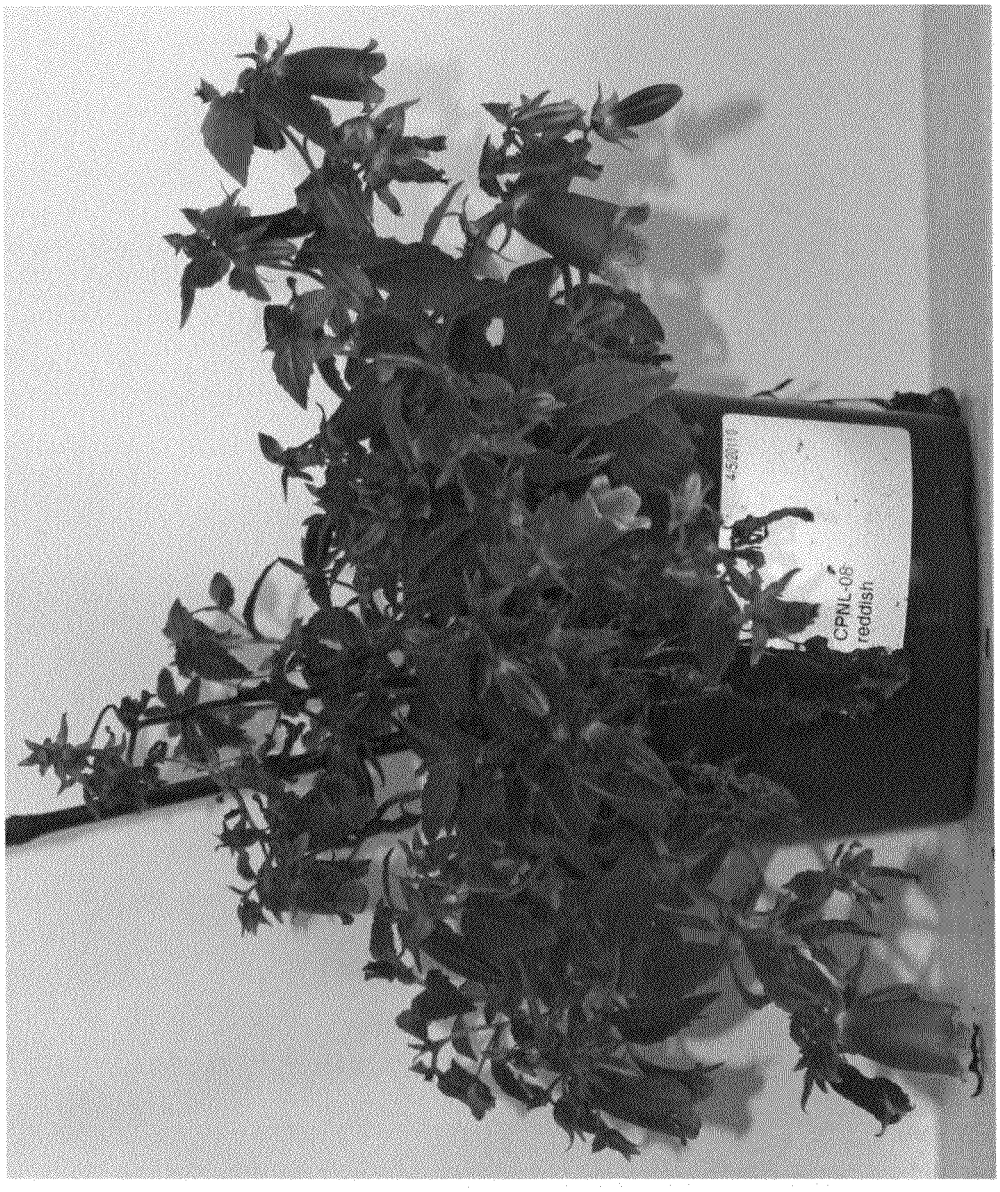
CPNL 05
reddish